(12) United States Patent
Rousseau

(10) Patent No.: US 10,765,546 B2
(45) Date of Patent: Sep. 8, 2020

(54) MODIFIED APPARATUS FOR FOOD EXTRACTION AND OBESITY TREATMENT

(71) Applicant: Ethicon, Inc., Somerville, NJ (US)

(72) Inventor: Robert Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 714 days.

(21) Appl. No.: 15/415,153

(22) Filed: Jan. 25, 2017

(65) Prior Publication Data

US 2018/0207014 A1 Jul. 26, 2018

(51) Int. Cl.
*A61M 1/00* (2006.01)
*A61F 5/00* (2006.01)
*A61M 39/02* (2006.01)
*A61J 15/00* (2006.01)

(52) U.S. Cl.
CPC ......... *A61F 5/0076* (2013.01); *A61J 15/0015* (2013.01); *A61M 1/008* (2013.01); *A61M 39/0247* (2013.01); *A61M 2039/0255* (2013.01); *A61M 2039/0285* (2013.01)

(58) Field of Classification Search
CPC ... A61F 5/0076; A61J 15/0015; A61M 1/008; A61M 2039/0255; A61M 2039/0285; A61M 2025/1063
See application file for complete search history.

(56) References Cited

U.S. PATENT DOCUMENTS

| | | | |
|---|---|---|---|
| 4,398,910 A | 8/1983 | Blake et al. | |
| 4,465,481 A | 8/1984 | Blake | |
| 4,501,264 A | 2/1985 | Rockey | |
| 4,641,653 A | 2/1987 | Rockey | |
| 4,763,653 A | 8/1988 | Rockey | |
| 7,648,479 B2 | 1/2010 | Solovay et al. | |
| 7,740,624 B2 | 6/2010 | Klein et al. | |
| 7,815,629 B2 | 10/2010 | Klein et al. | |
| 8,002,758 B2 | 8/2011 | Kamen et al. | |

(Continued)

FOREIGN PATENT DOCUMENTS

| | | |
|---|---|---|
| EP | 2412393 A1 | 2/2012 |
| EP | 2420261 A1 | 2/2012 |

(Continued)

OTHER PUBLICATIONS

International Search Report re: PCT/IB2018/050262 dated May 4, 2018.

(Continued)

*Primary Examiner* — Adam Marcetich
*Assistant Examiner* — Jessica R Arble

(57) ABSTRACT

A device that is inserted through the abdominal wall and into the digestive tract of a human is disclosed. The device may be placed through a method such as percutaneous endoscopic gastrostomy (PEG). The device includes a gastrostomy style structure that provides fluid communication with the external environment of the patient with the internal contents of the stomach. The device is produced with a series of slotted collection channels that preferentially, when connected to a source of negative relative pressure, directs a significant volume of the high calorie fluidic components of the chyme out of the digestive tract, preventing exposure to the absorptive tissues of the digestive tract when simple sugars and carbohydrates are consumed.

14 Claims, 14 Drawing Sheets

(56) References Cited

U.S. PATENT DOCUMENTS

| | | |
|---|---|---|
| 8,062,285 B2 | 11/2011 | Langloss et al. |
| 8,197,439 B2 | 6/2012 | Wang et al. |
| 8,282,623 B2 | 10/2012 | Klein et al. |
| 8,414,561 B2 | 4/2013 | Kamen et al. |
| 8,632,513 B2 | 1/2014 | Kamen et al. |
| 8,808,221 B2 | 8/2014 | Kamen et al. |
| 9,039,677 B2 | 5/2015 | Klein et al. |
| 9,055,995 B2 | 6/2015 | Solovay et al. |
| 9,151,646 B2 | 10/2015 | Kamen et al. |
| 2003/0040808 A1 | 2/2003 | Stack et al. |
| 2003/0225369 A1 | 12/2003 | McMichael et al. |
| 2004/0006331 A1* | 1/2004 | Shchervinsky ....... A61M 1/008 604/541 |
| 2004/0249360 A1* | 12/2004 | Spehalski ......... A61M 25/0133 604/523 |
| 2005/0283130 A1 | 12/2005 | Klein et al. |
| 2008/0033345 A1 | 2/2008 | Langloss et al. |
| 2008/0033364 A1 | 2/2008 | Kamen et al. |
| 2008/0033365 A1 | 2/2008 | Solovay et al. |
| 2008/0039809 A1 | 2/2008 | Kamen et al. |
| 2010/0241090 A1 | 9/2010 | Klein et al. |
| 2011/0071465 A1 | 3/2011 | Wang et al. |
| 2011/0190719 A1 | 8/2011 | Kamen et al. |
| 2012/0116161 A1* | 5/2012 | Nieman ............. A61B 1/00052 600/114 |
| 2013/0006166 A1 | 1/2013 | Klein et al. |
| 2013/0281985 A1* | 10/2013 | Querol Garcia .. A61M 25/0032 604/540 |
| 2013/0289474 A1 | 10/2013 | Kamen et al. |
| 2014/0275747 A1 | 9/2014 | Connor |
| 2014/0323955 A1 | 10/2014 | Kamen et al. |
| 2015/0038920 A1 | 2/2015 | Wojcik |
| 2015/0216696 A1 | 8/2015 | Klein et al. |
| 2015/0366692 A1 | 12/2015 | Wojcik |

FOREIGN PATENT DOCUMENTS

| | | |
|---|---|---|
| EP | 2422828 A1 | 2/2012 |
| EP | 2747833 A2 | 5/2013 |
| EP | 2747833 A4 | 5/2013 |
| EP | 2958608 A1 | 8/2014 |
| EP | 2958608 A4 | 8/2014 |
| EP | 2420261 B1 | 11/2014 |
| EP | 2389962 B1 | 12/2014 |
| EP | 2412393 B1 | 12/2014 |
| EP | 1784233 B1 | 8/2015 |
| EP | 2962708 A1 | 1/2016 |

OTHER PUBLICATIONS

Trout, et al "Dietary Influences on Gastric Emptying of Carbohydrate versus Fat in the Rat" Journal of Nutrition; 107: pp. 104-111 (1977).

* cited by examiner

MODIFIED APPARATUS FOR FOOD EXTRACTION AND OBESITY TREATMENT

BACKGROUND OF THE INVENTION

1. Field of the Invention

This invention is concerned with devices and methods useful for treating obesity. More particularly, this invention provides solutions that preferentially enable separation of high caloric fluidic components of chyme for diversion outside of the digestive tract.

2. Related Art

Obesity is a major US health issue and according to studies reported by the Centers for Disease Control and Prevention (CDC): the National Health and Nutrition Examination Survey (NHANES) and the National Health Interview Survey (NHIS), more than two-thirds (68.8 percent) of adults over 20 years of age are considered to be overweight or obese. Additionally, more than one-third (35.7 percent) of adults are considered to be obese and more than 1 in 20 (6.3 percent) have extreme obesity.

Additionally, the National Institute of Health reports that overweight and obesity are risk factors for type 2 diabetes, heart disease, high blood pressure, and other health problems such as nonalcoholic fatty liver disease (excess fat and inflammation in the liver of people who drink little or no alcohol), osteoarthritis (a health problem causing pain, swelling, and stiffness in one or more joints), some types of cancer: breast, colon, endometrial (related to the uterine lining), and kidney as well as stroke Not exclusively a US problem, worldwide obesity ranges are also increasing dramatically. The World Health organization reports that Worldwide obesity has more than doubled since 1980 and in 2014, more than 1.9 billion adults, 18 years and older, were overweight. Of these over 600 million were obese.

There is no single cause of all overweight and obesity and although the physiology and psychology of obesity are complex, the medical consensus is that the key contributing factor is an over intake of calories combined with reduced energy expenditures. There is no single approach that can help prevent or treat overweight and obesity. Treatment may include a mix of behavioral treatment, diet, exercise, and sometimes weight-loss drugs. In some cases of extreme obesity, weight-loss surgery may be an option.

Bariatrics is the field of medicine encompassing the study of the overweight condition, its causes, prevention and treatment. Bariatric surgery is a treatment for morbid obesity that involves alteration of a patient's digestive tract to encourage weight loss and to help maintain normal weight. Known bariatric surgery procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty.

There have been many attempts in the past to surgically modify patients' anatomies to attack the consumption problem by reducing the desire to eat. Stomach stapling, or gastroplasties, to reduce the volumetric size of the stomach, therein achieving faster satiety, were performed in the 1980's and early 1990's. Although able to achieve early weight loss, sustained reduction was not obtained. The reasons are not all known, but are believed related to several factors. One of which is that the stomach stretches over time increasing volume while psychological drivers motivate patients to find creative approaches to literally eat around the smaller pouch.

Two surgical procedures have successfully produced long-term weight loss: the Roux-en-Y gastric bypass and the biliopancreatic diversion with duodenal switch (BPD). Both procedures reduce the size of the stomach plus shorten the effective-length of intestine available for nutrient absorption. Reduction of the stomach size reduces stomach capacity and the ability of the patient to take in food. Bypassing the duodenum makes it more difficult to digest fats, high sugar and carbohydrate rich foods. One objective of the surgery is to provide feedback to the patient by producing a dumping syndrome if they do eat these food products. Dumping occurs when carbohydrates directly enter the jejunum without being first conditioned in the duodenum. The result is that a large quantity of fluid is discharged into the food from the intestinal lining. The total effect makes the patient feel light-headed and results in severe diarrhea. For reasons that have not been determined the procedure also has an immediate therapeutic effect on diabetes.

Although the physiology seems simple, the exact mechanism of action in these procedures is not understood. Negative feedback is provided from both regurgitation into the esophagus and dumping when large volumes of the wrong foods are eaten. Eventually, patients learn that to avoid both these issues they must be compliant with the dietary restrictions imposed by their modified anatomy. In the BPD procedure, large lengths of jejunum are bypassed resulting in malabsorption and therefore, reduced caloric uptake. In fact, the stomach is not reduced in size as much in the BPD procedure so that the patient is able to consume sufficient quantities of food to compensate for the reduced absorption. This procedure is reserved for the most morbidly obese as there are several serious side effects of prolonged malabsorption.

Laparoscopic techniques have been applied to these surgeries in an attempt to improve patient outcomes. While the laparoscopic techniques provide fewer surgical complications, they continue to expose these very ill patients to high operative risk in addition to requiring an enormous level of skill by the surgeon.

While surgery seems to be an effective answer, the current invasive procedures are not acceptable with these complication rates. Additionally, the devices that have been proposed in the literature, as well as the surgical approaches, provide a general approach of malabsorption of all nutritional components of the ingested foods. Further, the most favorable surgical procedure functions by the elimination of contact of ingested food with the absorptive tissues of the duodenum. The mechanism of the bypass, while not being fully understood, appears to limit the absorption of the carbohydrate and simple sugar components of the ingested food, as evidenced by the generally immediate reduction in the blood sugar levels of treated patients. Additionally, devices or newer surgical approaches that demonstrate this reduction of blood sugars are deemed successful, despite the potential creation of generalized mal-nutrition.

In the article "Dietary Influences on Gastric Emptying of Carbohydrate versus Fat in the Rat", by Trout et. al., published in the Journal of Nutrition; 107: 104-111, 1977, it was determined that "gravity tends to hold back the fat from leaving the stomach, allowing glucose in aqueous solution to be preferentially emptied" and further that "a sizable portion of the starch in starch-containing meals became suspended in water during and shortly after being ingested, and the starch suspension was then emptied from the stomach preferentially to fat-containing particulate matter". It would appear that this functionality of the natural separation of the glucose, or solubilized sugars, as well as the suspended starches and the subsequent acceleration of these components through the pyloric valve into the duodenum could be eliminated and thereby prevent the blood sugar from elevating while not inhibiting the absorption of the necessary dietary nutrients that are critical to cellular survival.

U.S. Pat. No. 4,398,910, to Blake, et. al. discloses a device for providing drainage from a surgical wound during the post-surgical period of healing.

US 2013/0281985, to Garcia, describes a three-lobe drainage hose useful in medical, surgical and/or post-surgical settings.

U.S. Pat. Nos. 4,501,264; 4,641,653 and 4,763,653; Rockey, discloses medical sleeve devices for placement in a patient's stomach. The medical sleeve described in these patents is intended to reduce the surface area available for absorption in the stomach without affecting the volume of the stomach nor will the device described isolate ingested food from stomach secretions. The medical sleeve is not configured to be deployed in a patient's small intestine and will not have an appreciable impact on the digestion of the ingested food.

US 2003/0040808, Stack et al. describes a satiation device for inducing weight loss in a patient includes a tubular prosthesis positionable at the gastro-esophageal junction region, preferably below the z-line. The prosthesis is placed such that an opening at its proximal end receives masticated food from the esophagus, and such that the masticated food passes through the pouch and into the stomach via an opening in its distal end. The pouch serves to delay the emptying of food into the stomach, thereby providing the patient a sense of fullness prior to filling the stomach.

US 2014/0275747 to Connor discloses a device that is comprised of two passages for food to travel through a patient's digestive tract, referred to as an Adjustable Gastrointestinal Bifurcation. The device has two openings that are regulated by a flow control member that may at least partially direct ingested food into either opening. The bifurcated device is comprised of two openings that are located at the superior end of the device just below the esophageal sphincter. The flow control member is capable of adjustment from a remote location and may direct food into either a passage that enables little absorption of nutrients or a second passage that does not limit the absorption of nutrients. While the device can divert various food types, it requires a conscious effort on behalf of the user or physician to set the diversion pathway into the correct location for the specific food type that has been ingested. An alternative form of the device requires the implantation or use of a remote sensor within the upper GI tract to sense the type of food being ingested to direct the flow control member. This would require the presence of an invasive foreign object within the upper GI tract, particularly the oral cavity, which would be intolerable to the patient.

In U.S. Pat. Nos. 7,740,624; 7,648,479; 7,815,629; 8,002,758; 8,062,285; 8,282,623; 9,039,677; 9,055,995, Klein et al. describe devices for the extraction of ingested food through an aperture in the skin of the patient. The devices described are based upon the reverse functionality of a traditional gastrostomy tube that passes percutaneously through the abdomen of the patient. U.S. Pat. No. 8,282,623 provides embodiments wherein the devices are provided with a fenestrated tube that is positioned within the stomach of the patient. The fenestrated tube transitions into a fully enclosed tubular structure that exits the stomach of the patient through the abdominal wall and terminates at a valve apparatus that facilitates communication with an external source of siphoning negative relative pressure or connection with a pump unit. This unit enables the reduction of at least a portion of the ingested material within the stomach and enables passage of the ingested material through the abdominal wall of the patient into an appropriate disposal container. While the device provides the means for reducing the quantity of ingested materials, the device suffers from the limitations of clogging due to large particles of ingested materials either lodging in the fenestrations or through the induction of particles within the inner bore of the tube at various locations including, but not limited to, the location of valve connection fittings. Further, the use of the fenestrated tube suffers from the potential to adhere to the local tissues and may produce tissue damage as a result of the sustained application of low pressure to the local tissue. The device as described also suffers from the limitation of other mass procedures or devices in that there is no selectivity with regards to the type of ingested materials being removed. Any ingested particle, as long as it fits within the fenestrations or proximal end of the tube, are subject to removal. Therefore, favorable food materials that are not digested such as those high in minerals, proteins and vitamins are as likely to be removed as the low quality materials that are high in caloric content due to the presence of simple sugars and starches. This limitation ultimately limits utility as the patient only reduces the total quantity of ingested materials, as is done through behavioral portion control, as opposed to enabling the retention of favorable food stuffs and the elimination of poor quality food stuffs.

There remains the need to provide a device that is capable of redirecting the most damaging components of food that is ingested that is reversible, does not inhibit the digestion of healthy components of ingested food, does not rely on patient inputs to function properly and provides negative biological feedback to inhibit the ingestion of simple sugars and carbohydrates.

SUMMARY OF THE INVENTION

The present invention relates to methods and devices for directing a significant volume of the high calorie fluidic components of the chyme out of the digestive tract, preventing exposure to the absorptive tissues of the digestive tract when simple sugars and carbohydrates are consumed.

In one embodiment, a device is claimed comprising:
a) a channeled collection element having a longitudinal axis, a distal end and a proximal end;
b) at least one slot formed in the channeled collection element, said slot parallel to the longitudinal axis of the channeled collection element and sized to permit entrance into the collection element of solubilized sugars or dispersed starches; and
c) a port or a port/valve assembly in fluid communication with the distal end of the channeled collection element.

Another embodiment of the invention relates to a method of extracting fluids rich in solubilized sugars and dispersed starches from a patient's gastrointestinal tract comprising the steps of:
a) inserting into the stomach of the patient a device comprising:
i. a channeled collection element having a longitudinal axis, a distal end and a proximal end;
ii. at least one slot formed in the channeled collection element, said slot parallel to the longitudinal axis of the channeled collection element and sized to permit entrance into the collection element of solubilized sugars or dispersed starches; and
iii. a port or a port/valve assembly in fluid communication with the distal end of the channeled collection element;
b) connecting to the port or port/valve assembly in fluid communication with the distal end of the channeled collection element a disposal tube; and
c) withdrawing fluid from the patient's stomach to a point external to the patient through the disposal tube.

DETAILED DESCRIPTION OF PREFERRED EMBODIMENTS OF THE INVENTION

As used herein, the term "proximal" shall refer to the part or portion of a device that would be closest to the center of the anatomy or closest or inside of the organ of interest (in this instance, the stomach) when such device is in use. Likewise, as used herein, the term "distal" shall refer to the part or portion of a device that would be furthest from the center of the anatomy or organ of interest when such device is in use.

Figure 1:
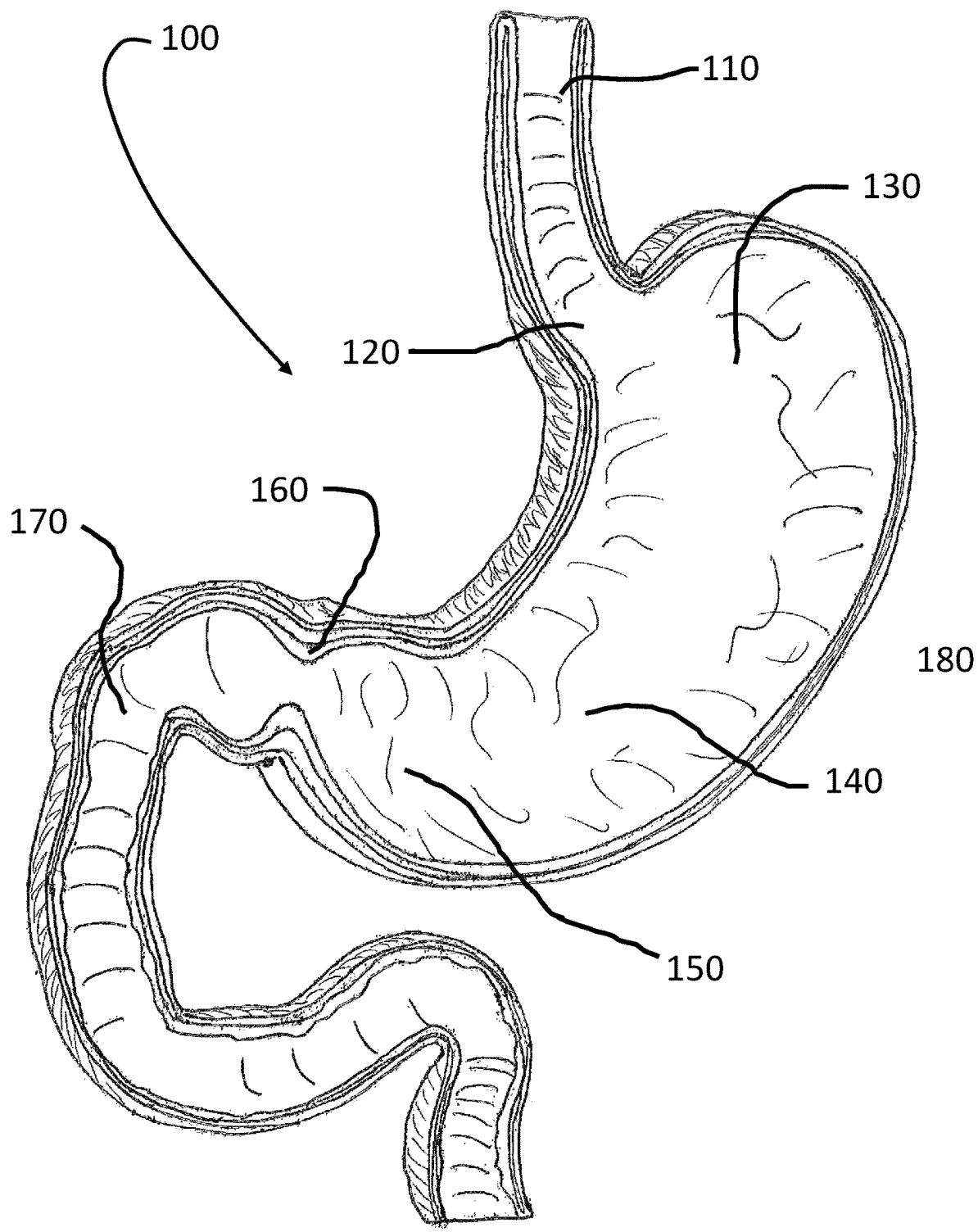
FIG. 1 depicts elements of the digestive tract.

Referring to FIG. 1, the upper middle portion of the human gastrointestinal tract 100 is illustrated. The esophagus 110 leads to the lower esophageal sphincter 120. The lower esophageal sphincter is located at the entry point into the stomach 180 and serves to admit ingested particles of food into the stomach and to subsequently form a seal, when constricted, to prevent the regurgitation of food particles and digestive fluids into the esophagus during the muscular contractions associated with the digestive process. The food enters the stomach near the fundus 130 and is subjected to the digestive secretions of the stomach lining. As the digestive contractions of the fundus occur, the food passes towards the antrum 140 and ultimately passes into the pylorus 150 of the stomach where it is subjected to strong contractions and the liquefied portion of the semi-digested material, or chyme, is passed into the duodenum 170 through the dilation of the pyloric valve 160.

Figure 2:
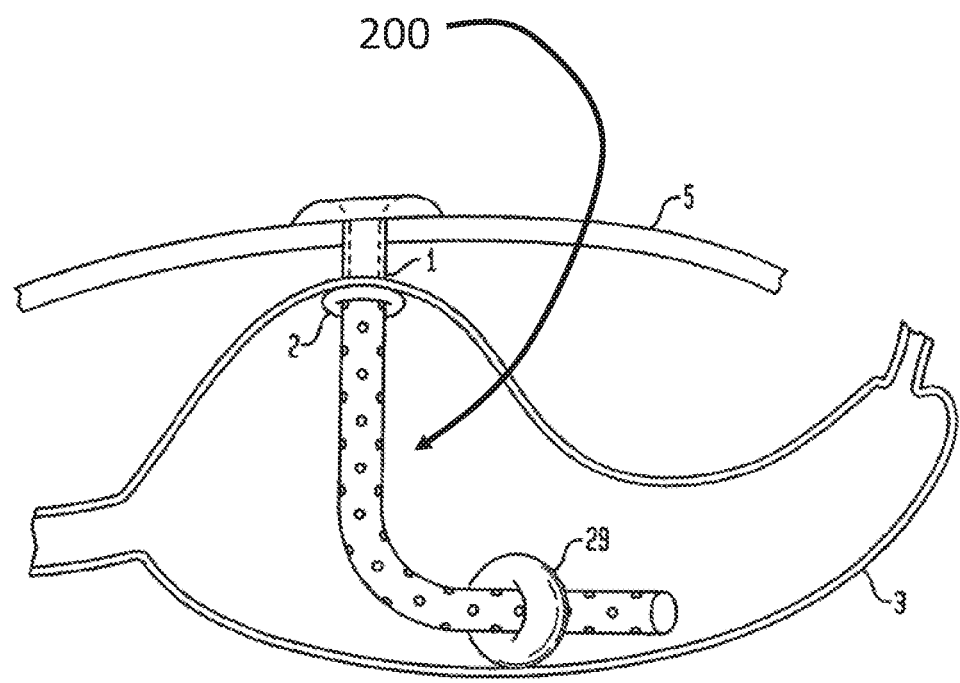
FIG. 2 depicts one embodiment of a prior art device.

Referring to FIG. 2, an embodiment is illustrated of a prior art gastrostomy extraction device 200. This device is further described in U.S. Pat. No. 8,282,623. Device 200 provides fluid communication between the internal volume of stomach 3 and the external environment as it passes through skin 5 of the patient. Tube 1 passes through the space between the wall of the stomach and the external surface of the patient's skin on their abdomen. Device 200 is provided with anchor 2 which may be in the form of an inflatable or flexible anchor that is deployed during the placement of device 200 in the abdomen. Device 200 is optionally provided with inflatable balloon element 29 which may be utilized during the course of ingesting food to help occupy the volume of the stomach and to limit the capacity of the stomach.

Figure 3:
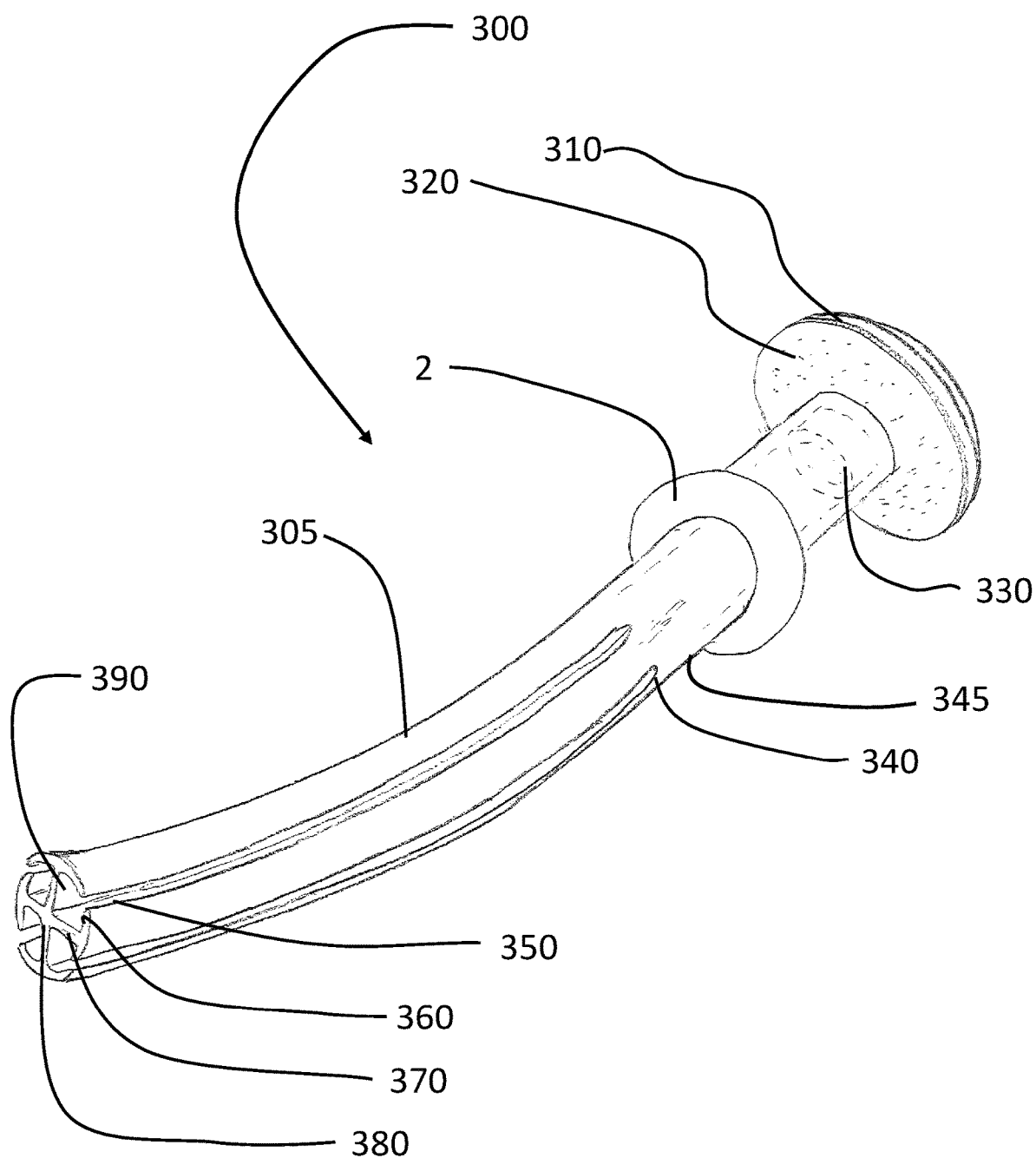
FIG. 3 depicts one embodiment of the device of this invention.

Referring to FIG. 3, extraction device 300 is illustrated. Device 300 comprises channeled collection element 305, anchor 2, a port and valve assembly 310, an optional adhesive backing 320, and connector 330 providing fluid communication between collection element 305 and port/valve assembly 310. In one embodiment, the cross section of channeled collection element 305 may be provided in a generally cruciform profile 380. Radial elements 370 extend outwardly from the center portion of the cruciform structure and bisect individual outer overhanging perimeter elements 360. While the cruciform embodiment is illustrated, alternative geometries such as bisected circular, rectangular, square or polygonal forms are also contemplated. Triangular forms are also contemplated wherein the profile of channeled collection element 305 is created with three radial elements and accompanied with pairs of three overhang elements to provide three collection channels as opposed to the four channels. A closed form of collection element 305 is also contemplated wherein collection element 305 comprises a contiguous perimeter that is interrupted by a singular slot. The use of radial extension elements are not necessary in these collection elements, however, any of the disclosed collection elements may further comprise additional closed channels within the collection element that may serve the purpose of fluid communication for activities such as providing an inflation conduit for proximally located inflation elements, or, alternatively, may be utilized to receive instrumentation such as guide wires, endoscopic instrumentation or catheter style devices.

Figure 4:
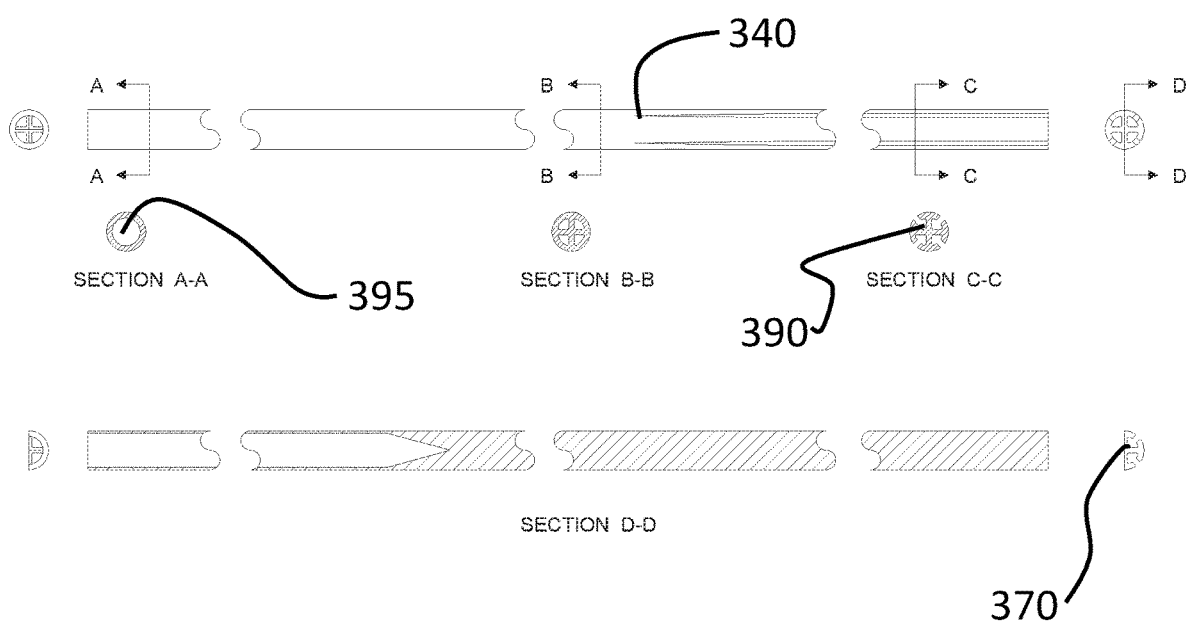
FIG. 4 illustrates cross-sectional views of a preferred collection element.

The embodiment illustrated in FIG. 3 is formed with multiple overhanging elements 360 that terminate proximate to the next overhanging element 360. This spacing of the overhanging elements form external channels (slots) 350 that extend at least partially along the external wall of collection element 305 to a termination point 340 where collection element 305 becomes continuous 345 about the perimeter of the collection element 305. Typically, the channels (slots) 350 will comprise from 40% to 90%, preferably 60% to 80%, most preferably 70% of the length of collection element 305. Preferably, the channels (slots) are from 0.025 mm wide to 1.5 mm wide, and more preferably channels that are 0.25 mm to 0.85 mm in width, and most preferably 0.400 mm in width to enable the desired particulate selectivity. Additionally, proximate this location of the termination of the external channels 350, the inner forms of radially extending elements 370 terminate thereby forming a fully hollow cylindrical element 345 near the distal end of collection element 305. As can be seen in the illustrated embodiment, inner channel elements 390 are formed by the intersection of radially extending elements 370 with overhanging perimeter elements 360. The inner channel elements 390 extend from the proximal end of collection element 305 to the distal termination point of the radially extending elements where the discrete inner channel elements 390 merge together to form the full hollow cylindrical element 395 as shown in the two dimensional and sectional illustration FIG. 4

Referring again to FIG. 3, a portion of collection element 305 near the distal end of the collection element passes through, or is assembled with, the anchor element 2. Anchor element 2 may be inflatable or may utilize a collapsible, semi-spherical form that provides the functionality of maintaining the deployed collection element 305 in position within the stomach. The distal end of collection element 305 is designed to interface with port/valve element 310. The use of a tapered connector 330 to join collection element 305 to port/valve element 310 is illustrated, although threaded or luer lock style connectors may be used. Port/valve element 310 may be provided with an optional adhesive backing 320 that is intended to maintain port/valve 310 in sealed contact with the local skin surface. Further, the adhesive backing may include an anti-microbial component, such as Triclosan, to minimize the possibility of infection forming at the site of the penetration of the tube as well as prevent the potential colonization of the external surface of the collection element after insertion. Port/valve element 310 serves as the point of interconnection with an external source of negative relative pressure during the time of an extraction activity and provides the sealed valve function during times of normal patient daily activity.

The collection element 305 may be formed of elastomeric materials such as silicone, natural rubber, elastomeric resins such as Hytrel®, produced by DuPont™, elastomeric polyurethanes, etc.

The resins that are utilized may be formed into the final form of the collection element through the use of injection molding, extrusion, 3D printing or other suitable methods.

The extruded form of the collection element may be produced in accordance with the methodology disclosed in U.S. Pat. No. 4,465,481. In the case of extrusion of the collection element, the collection element having four lumens can be formed with an extrusion die having a linearly movable first die form consisting of four prongs adjacent the outer edge of the die cavity, forming in the melted flowable polymer the four lumens of the collection element segment. As the first die form is withdrawn from the die cavity, a cylindrical die mandrel for forming in the melted flowable polymer the central cavity of the extension tube segment is brought into the die cavity. The very short transition tube segment is formed when both the first die form and the cylindrical die mandrel are simultaneously positioned in the die cavity for a brief time during the extrusion process.

To form the portion of the collection element having a single lumen, a single die pin is provided in the die cavity. To form the drain segment of the catheter, this pin is positioned adjacent the edge of the die cavity, where the pin forms in the melted flowable polymer the single longitudinal lumen. As the extrusion process continues, the pin is moved toward the center of the die cavity, forming the transition tube segment. At the center of the die cavity the pin is a die mandrel around which the extension tube formed.

Figure 5:
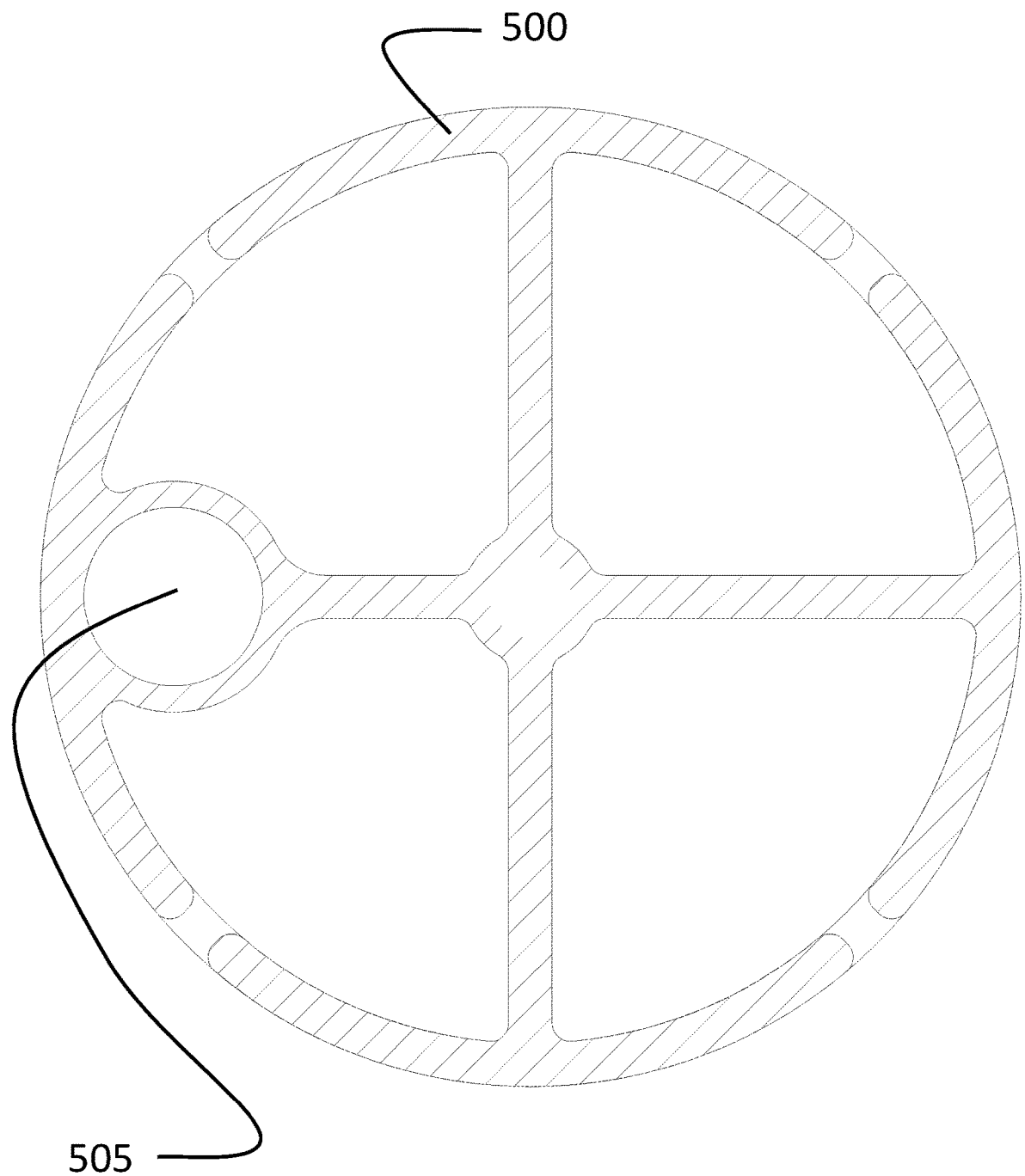
FIG. 5 depicts an optional enclosed lumen useful in various embodiments of the collection element.

Referring to FIG. 5, an alternative embodiment of the collection element 500 may be produced with at least one distinct enclosed lumen 505 that extends along the length of the collection element and is separate from the other lumens within the collection element. The distinct enclosed lumen 505 is may be used for inflation or to receive a spring form element enabling the collection element to main a desired shape or form. The distinct lumen 505 may be and is typically formed through the introduction of an additional die pin within the extrusion die.

Figure 6:
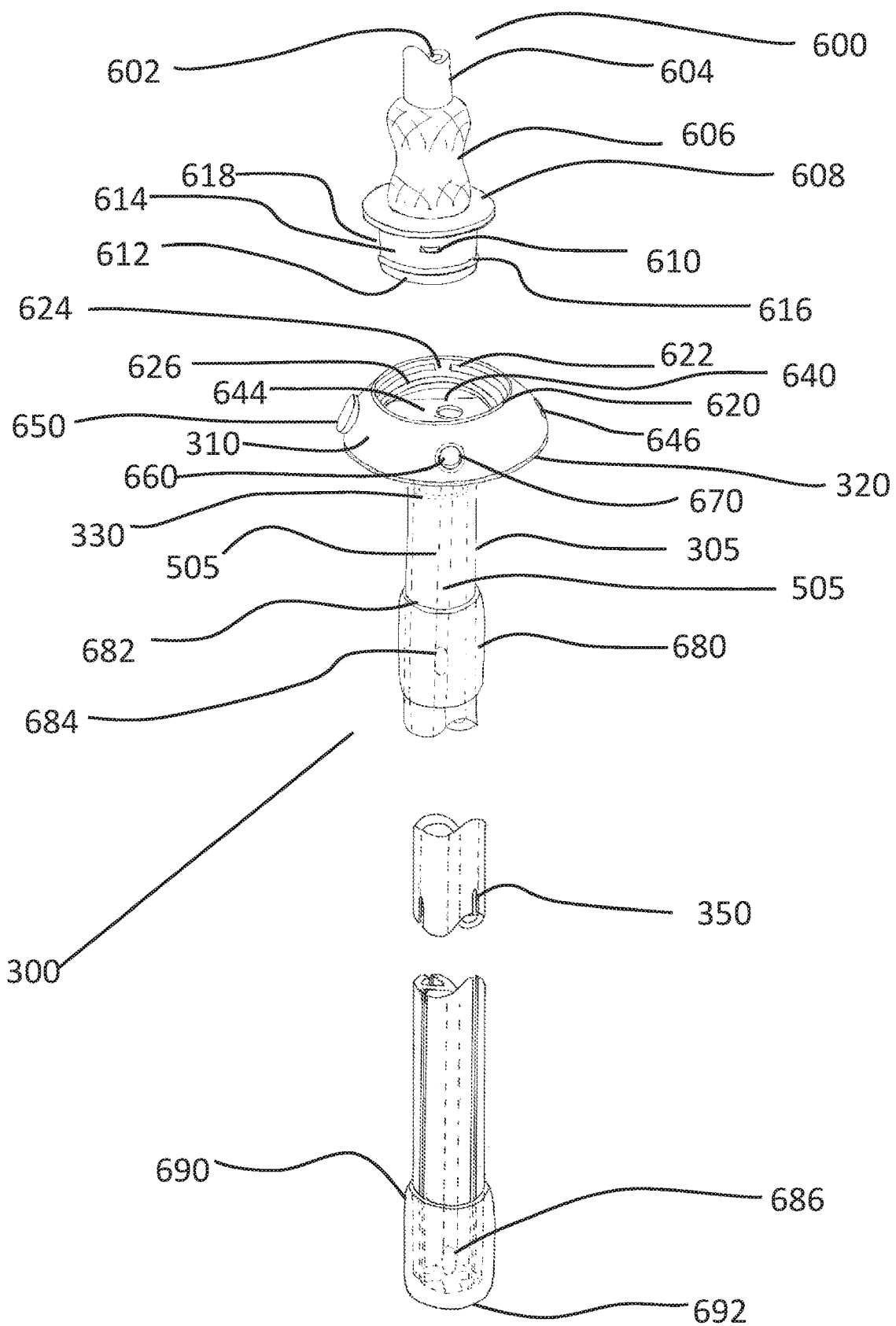
FIG. 6 illustrates a semi-exploded view of one embodiment of the device of this invention.

Referring to FIG. 6, a semi-exploded view is provided of the extraction device 300 and the distal end of a suitable disposal tube assembly 600. The disposal tube 604 is attached to the fitting 618 through the use of a barbed fitting, not shown, located on the distal end 602 of the fitting 618. The proximal end 612 of the fitting is produced with a main barrel diameter 614 that is sized to fit within the receiver bore 640 of the port/valve assembly 310. A locking tab 610 extends radially outward from the main barrel diameter 614 and is sized to pass through the receiver notch 624 within the receiver bore 640. There is an inwardly extending ring engagement element 622 that extends about the inner perimeter of the receiver bore 640 and is disrupted by two of the receiver notches 624. A compressible seal element 616, such as an O-ring, is mounted on the proximal end of the main barrel diameter 614. There is a flange element 608 located distally to the main barrel diameter 614. The flange element 608 is intended to abut the distal face 620 of the port/valve assembly 310 when the components are assembled for evacuation of the stomach contents through the device. An optional gripping element 606 is included for ease of handling during assembly and disassembly of the disposal tube assembly 600 to the port/valve assembly 310. The receiver bore is produced with an optional seal channel 626 that will mate with the compressible seal element 616. The seal channel provides an additional engagement feature to ensure that the fitting remains engaged with the valve/port assembly 310. The port/valve assembly 310 is produced with a valve gate button 650 that is utilized to open and close the valve gate 644 (illustrated as a hidden feature). Additionally, on the opposite side of the valve/port assembly 310 there is a latch release lever 646. Included in the port/valve assembly 310 is an inflation port 670 that includes a silicone septum 660. The collection element 305 is mounted to the valve/port assembly through the use of the barbed fitting 330 located on the proximal side of the valve/port assembly 310. An inflatable anchor 680 is bonded about the perimeter of the collection element 305 as shown at the joint 682 formed between the inflatable anchor 680 and the collection element 305. Further, the inner volume of the inflatable anchor 680 is in direct fluid communication with the inner volume of the distinct lumen 505 through the use of the skived penetration 684 of the distinct lumen 505. Alternatively, punctures, cuts or punched openings may be utilized to provide a hole in the wall of the distinct lumen 505. Shown is the inclusion of a secondary inflatable float element 690 located on the proximal end of the collection element 305. The inflatable float element 690 is bonded to the proximal end of the collection element. Additionally, the inner volume of the inflatable float element 690 is in direct fluid communication with the distinct lumen 505 through the use of a skived penetration 686 of the collection element 305 distinct lumen 505. The proximal end of the distinct lumen 505 is provided with a sealed end 692 to enclose the extruded distinct lumen 505. The sealed end 692 may include the closure of the other lumens of the collection element as well and may be achieved through the use of adhesives, thermal fusion, mechanical clamping or combinations of the forgoing methods of achieving a hermetic seal of the lumen.

Figure 7:
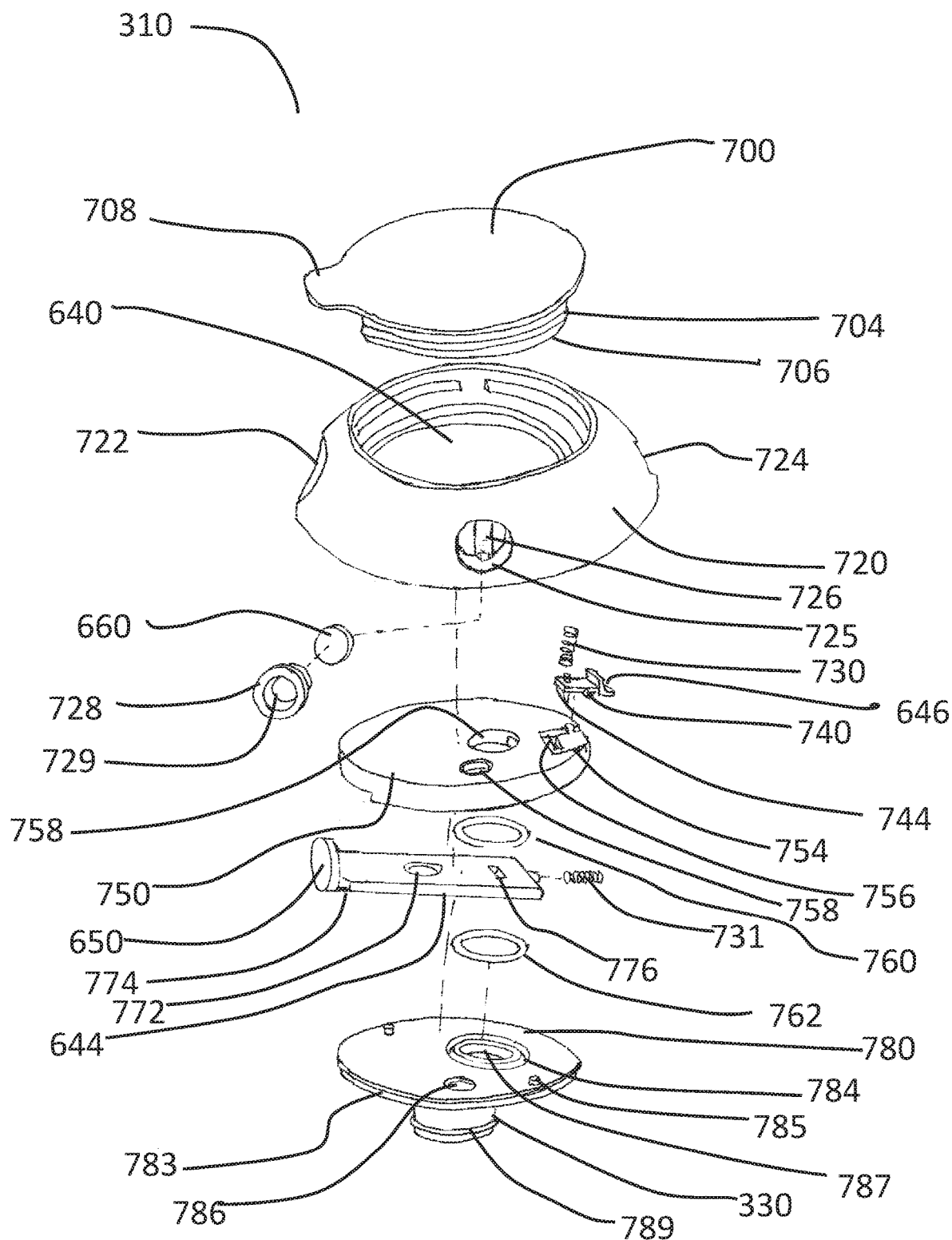
FIG. 7 is a detailed view of one embodiment for valve/port assembly for the device of this invention.

Referring to FIG. 7, an exploded view of the valve/port assembly 310 is presented. The port valve/assembly is comprised of an elastic plug element 700, an external body element 720, a silicone septum 660, a septum retention ring 728, a latch release lever 646, a latch return spring 730, a gate guide body 750, an upper O-ring 760, a valve gate 644, a valve gate return spring 731, a lower O-ring 762 and a base element 780. The elastic plug element 700 is intended to be inserted into the distal end of the receiver bore 640 to provide a smooth surface to the valve/port when it is not in use. The elastic plug element is formed with a pull tab extension 708 that is graspable by the use to facilitate removal. Additionally, the proximal plug element 706 is sized to fit within the receiver bore 640. There is a rib like element 704 that extends about the perimeter of the proximal plug element 706. The rib like element 704 is sized to mate with the seal channel 626 or may be sized to only engage with the inwardly extending ring engagement element 622. The external body element 720 is produced with a valve gate button bore 722 intended to mate with the valve gate button 650. On the opposing side of the external body element 720 is the latch release lever receiver slot 724. The latch release lever 646 extends through latch release lever slot 724 to be accessible to the user. The external body element 720 is also produced with a septum receiver bore 725 that includes a vertical cross bore 726 that exits through the base of the external body element 720. The silicone septum 660 is placed within the septum receiver bore 725 and is held in place by the septum retention ring 728. The septum retention ring 728 is bonded to the external body element through the use of adhesives or energy based fusion of the septum retention ring 728 to the external body element 720. Alternatively, mechanical means such as interference fits may also be utilized to maintain the septum retention ring in contact with the external body element 720. The septum retention ring 728 is produced with a through bore 729 to enable access to the septum 660 with a piercing inflation element such as a needle.

The distal end of the latch return spring 730 is inserted into a receiver bore, not shown, within the proximal end of the external body element 720. The latch release lever is produced with two cylindrical extension elements 740 that extend perpendicular to the central axis of the latch release lever 646 and serve as hinge like features. The cylindrical extension elements are mated to two extension element receiver wells 754 located in the distal surface of the gate guide body 750 as well as the latch prong 744 passing through the gate guide body slot 756. The latch release lever 646 is engaged with the proximal end of the latch release spring 730 and the latch release lever and gate guide body elements are inserted into the distal opening of the external body element 720. The guide body is oriented to align the inflation bore 758 with the vertical cross bore 726. The gate guide body 750 may be bonded into the external body element 720 through the use of adhesives, fusion or other mechanical means. The upper O-ring 756 is placed within the receiver well, not shown in the proximal side of the gate guide body 750. The valve gate return spring 731 is assembled onto the end of the valve gate 644 and the assembly is placed into the proximal side of the gate guide body 750 with the valve gate button 650 passing through the valve gate button bore 722 and with the valve gate shoulder 774 in abutment with the inner surface of the external body element 720. The lower O-ring is placed within the lower O-ring receiver channel 784 located within the base element 780. The base element guide pins 785 are aligned and assembled to the receiver holes, not shown, in the proximal side of the gate guide body 750 and is bonded to the external body element about the perimeter 783 through the use of adhesives, or fusion or other mechanical means such as snap fit elements. In this position, the base element inflation bore 786 is in sealed alignment with the inflation bore 758 in the gate guide body 750. The tapered connector 330 extends proximally from the base element 780. The tapered connector 330 may include a barbed style ring 789 about the perimeter of element.

In order to utilize the assembled extraction device 300, a stoma is formed through the abdominal wall of the patient that extends into the anterior surface of the stomach. The device is removed from the associated packaging and the release liner covering the optional adhesive backing 320 is removed. The proximal end of the extractor device 300 is inserted into the stoma and into the stomach until the adhesive backing 320 on the proximal surface of the port/valve assembly 310 is in abutment with the anterior surface of the abdomen. Once the extractor device 300 is in position, a source of an inflation gas such as air, carbon dioxide or nitrogen is connected to the extractor device 300 through the use of an inflation needle that pierces the silicone septum 660. The inflation gas enters the distinct lumen 505 of the collection element through the assembled vertical cross bore 726 the inflation bore 758 and the base element inflation bore 786 where it enters the distal opening of the distinct lumen 505. The inflation source remains engaged until the inflatable anchor 680 and the inflatable float element 690 are completely filled. Once the necessary pressure has been achieved, the inflation source is removed.

In use, the device 300 is accessed by the patient upon the completion of the meal and the necessary ingestion of the specified quantity of water or other potable fluid. The elastic plug element 700 is removed from the port/valve assembly 310. The disposal tube 600 is then attached to the port/valve assembly 310 by aligning the locking tabs 610 with the receiver notches 624 within the receiver bore 640 of the port/valve assembly 310. The fitting is pressed proximally into port/valve assembly 310 until it is fully seated. The disposal tube fitting is then rotated while the port/valve assembly is held in position thereby forcing the locking tabs 610 under the ring engagement element 622. The valve gate button 650 is depressed thereby forcing the valve gate 644 laterally until the latch prong 744 engages with the valve gate receiver slot 776. In this position, the exit port 787 in the base element 780, the gate port 772 and the gate guide body port 758 are in full alignment thereby enabling fluid communication between the disposal tube 600 and the collection element 305. A source of suction, such as a siphon or external pump is activated to then remove the desired quantity from the stomach. Upon completion of the extraction, the valve gate 644 is closed by the depression of the latch release lever 646 which removes the latch prong 744 is withdrawn from the valve gate receiver slot 776 thereby allowing the valve gate to be forced laterally by the valve gate return spring 731. Upon closure of the valve gate 644, the disposal tube 600 is removed from the port/valve assembly by rotating the disposal tube fitting in the opposite direction from what was done during installation to allow the locking tabs 610 to align with the receiver notches 624 and subsequent pulling of the fitting. The elastic plug element 700 is then re-installed until the next extraction.

Figure 8:
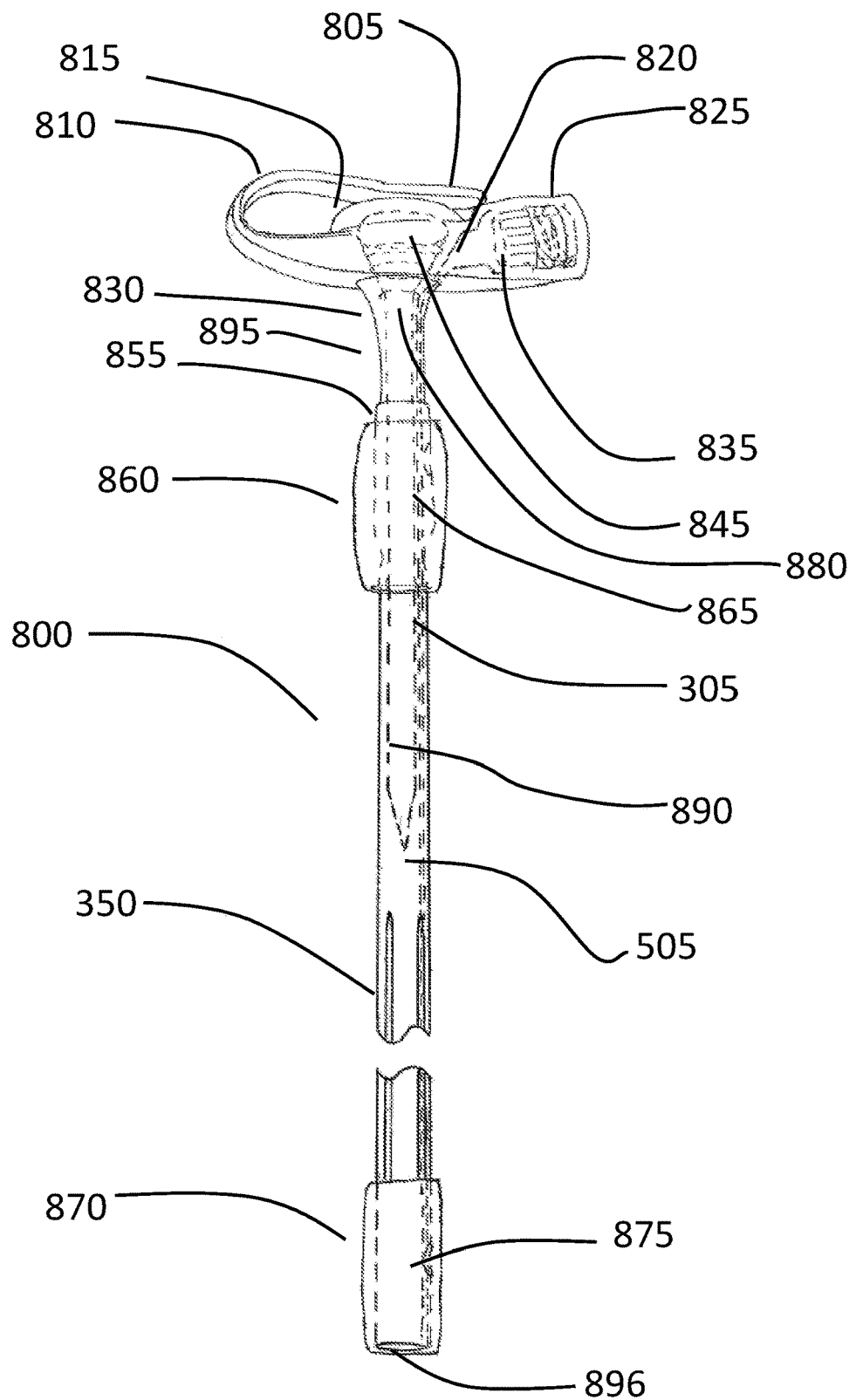
FIG. 8 illustrates a valveless embodiment for the device of this invention.

Referring to FIG. 8, an alternative embodiment of a simplified extractor device 800 is illustrated. Unlike the previously disclosed extractor device 300, the simplified extractor device 800 is produced without a valve mechanism. The collection element 305 is the same as that produced for the extractor device 300 previously described and is comprised of the extruded element with external channels 350 that transition distally into a solid form with a central lumen 890. The distinct lumen 505 that is in fluid communication with the inflatable anchor element 860 as well as the inflatable float element 870 and the distal lumen 880 through the skived penetrations in the wall of the distinct lumen 505 shown as the distal skive 865 and the proximal skive 875. The distal lumen 880 intersects with the lateral lumen 820 which is in abutment with the silicone septum 835 contained within the inflation channel access port 825. The central lumen 830 of the simplified extractor device is accessible through the upper port 815. When the device is not in use, the upper port 815 is maintained in a sealed condition through the use of the closure plug 845 which is produced with a graspable extension flange 805. A tether element 810 is incorporated into the distal edge of the closure plug 845. The simplified extractor device 800 may be produced through the use of subassemblies that are bonded together within the distal joint 855. The distal joint is a cylindrical formed element that is sized to fit over the proximal end of the upper device base extension 895 and the distal end of the collection element 305. The upper device base extension 895 and the distal end of the collection element 305 are held in tight abutment within the distal joint and may be fused together through the use of energy based bonding methods as well as adhesives or in the crudest form through the use of mechanical fittings such as barbed fittings within each of the lumens. The proximal end of the distinct lumen 505 is provided with a sealed end 896 to enclose the extruded distinct lumen. The sealed end 896 may include the closure of the other lumens of the collection element as well and may be achieved through the use of adhesives, thermal fusion, mechanical clamping or combinations of the forgoing methods of achieving a hermetic seal of the lumen.

Figure 9:
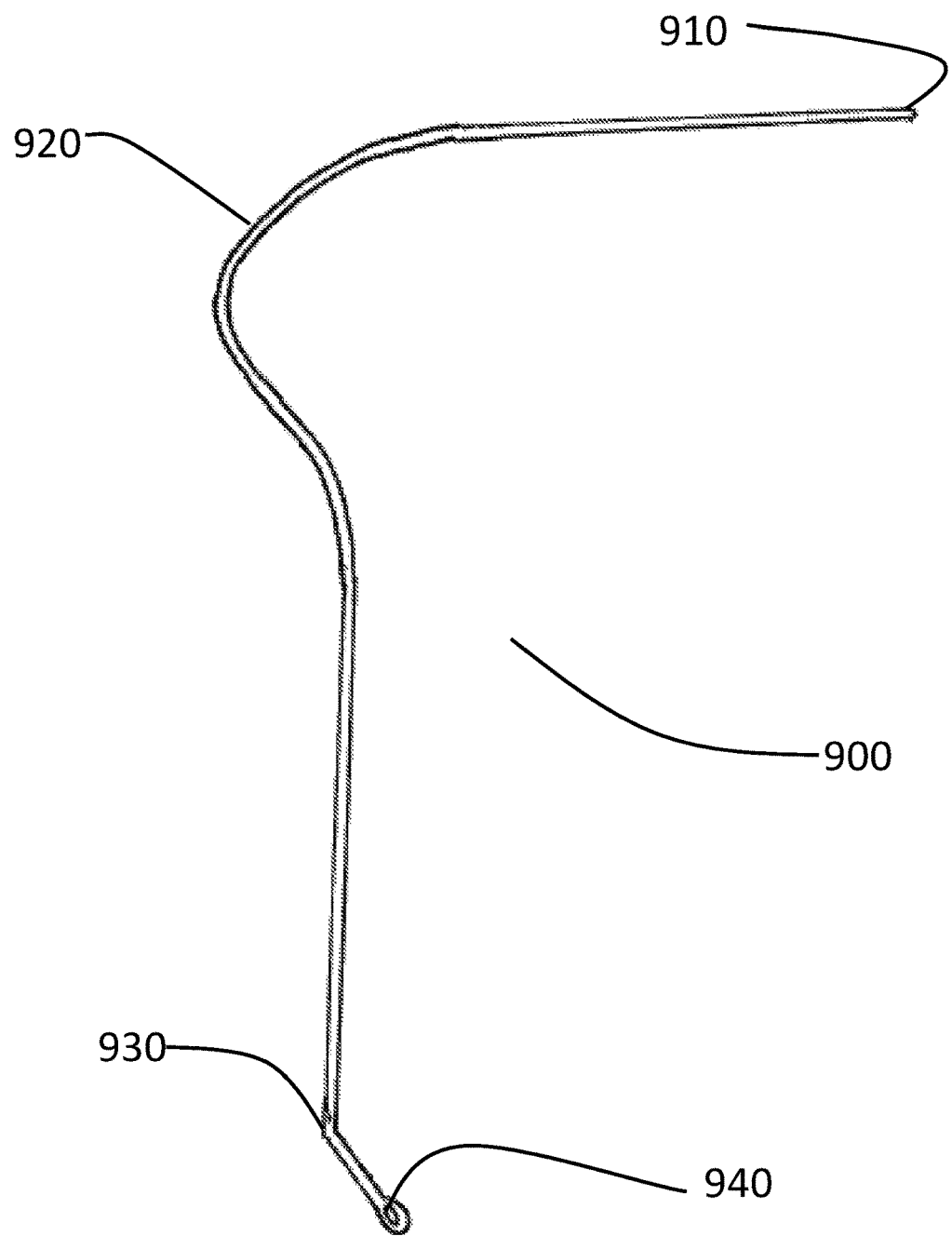
FIG. 9 depicts a shaping element suitable for use with the device of this invention.

Referring to FIG. 9, shaping element 900 is shown. The shaping element is formed of a resilient material and is produced with a pre-determined shape as shown. The proximal end of the shaping element 910 is produced with a spherical or blunted shaped tip. The distal end of the shaping element includes a graspable element 940 that may be in the form of a loop. Alternatively, the graspable element 940 may also be simple form such as a flange or a textured surface such as a knurled surface that is capable of facilitating engagement and handling of the distal end of the shaping element 900. The shaping element is produced with a central radius profile 920 and also a distal bend 930. The shaping element may be produced out of any material that can serve the purpose of producing a spring element such as polymeric materials or metals such as 300 series stainless steel, hardened 400 series stainless steel or more preferably a shape memory material such as Nitinol. The use of Nitnol wire that is from 0.2 mm-1.5 mm in diameter is suitable, however, larger diameter wire or alternative wire forms such as ribbon may also be utilized.

Figure 10:
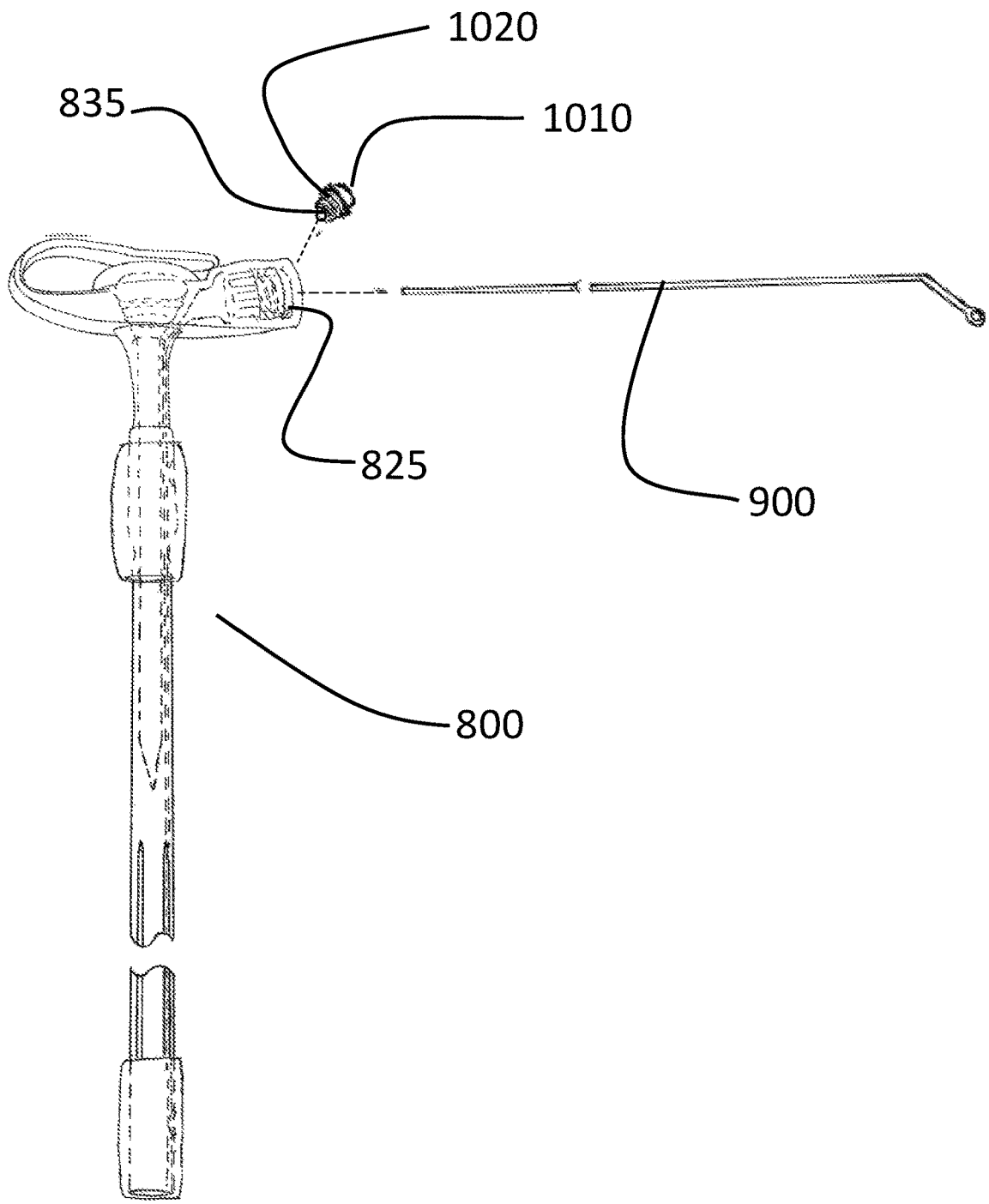
FIG. 10 illustrates the use of a shaping element in conjunction with one embodiment of the device of this invention.

Referring to FIG. 10, the insertion of the shaping element 900 into the simplified extractor device 800 is illustrated. In use, the proximal end 1025 of the simplified extractor device 900 is inserted into the stoma in the patient's abdominal wall until the distal face 1035 is fully seated against the skin of the abdomen. The inflation channel access port plug 1010 is removed from the inflation channel access port 825. The plug is removed by unscrewing from the inflation channel access port 825 and the threads 1020 are shown on the inflation channel access port plug 1010. The silicone septum 835 is contained within the inner bore of the inflation channel access port plug 1010 and can be pierced by a needle passed through the inner lumen of the inflation channel port access plug 1010. Once the plug is removed from the inflation channel access port 825, the shaping element 900 is straightened out temporarily and the proximal end 910, or blunt end, of the shaping element 900 is inserted into the inflation channel access port 825. The shaping element is inserted fully until the graspable element 940 is seated within the lateral lumen 820.

Figure 11:
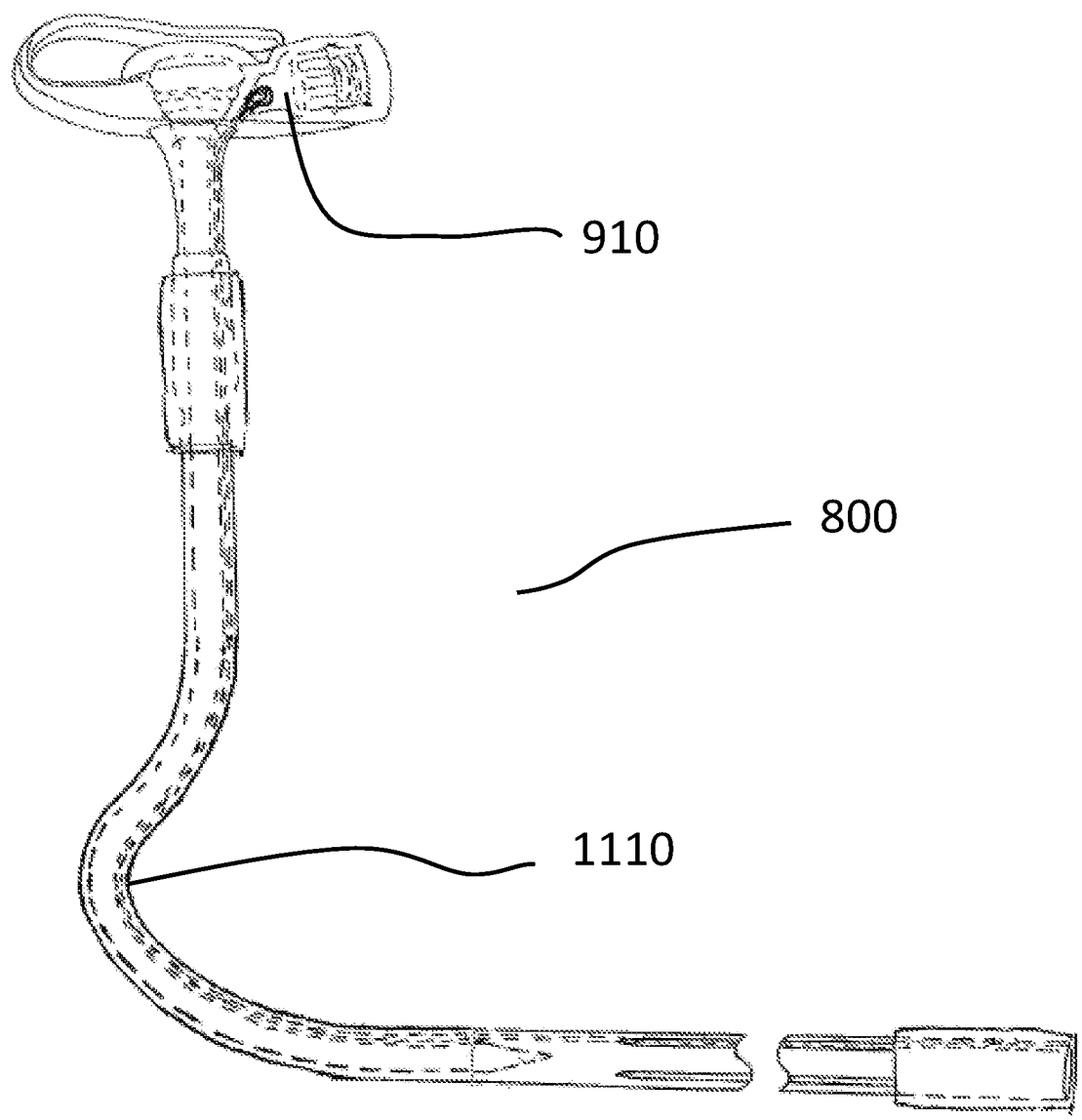
FIG. 11 depicts a shaping element deployed within one embodiment of the device of this invention.

Referring to FIG. 11, the simplified extraction device 800 is shown with the shaping element 900 fully in place within the distinct lumen 505 and the inflation channel access port plug 1010 screwed back into place thereby containing the shaping element 900 within the simplified extraction device 800. The shaping element forces the shape of the collection element into a semi-"S" form 1110.

Figure 12:
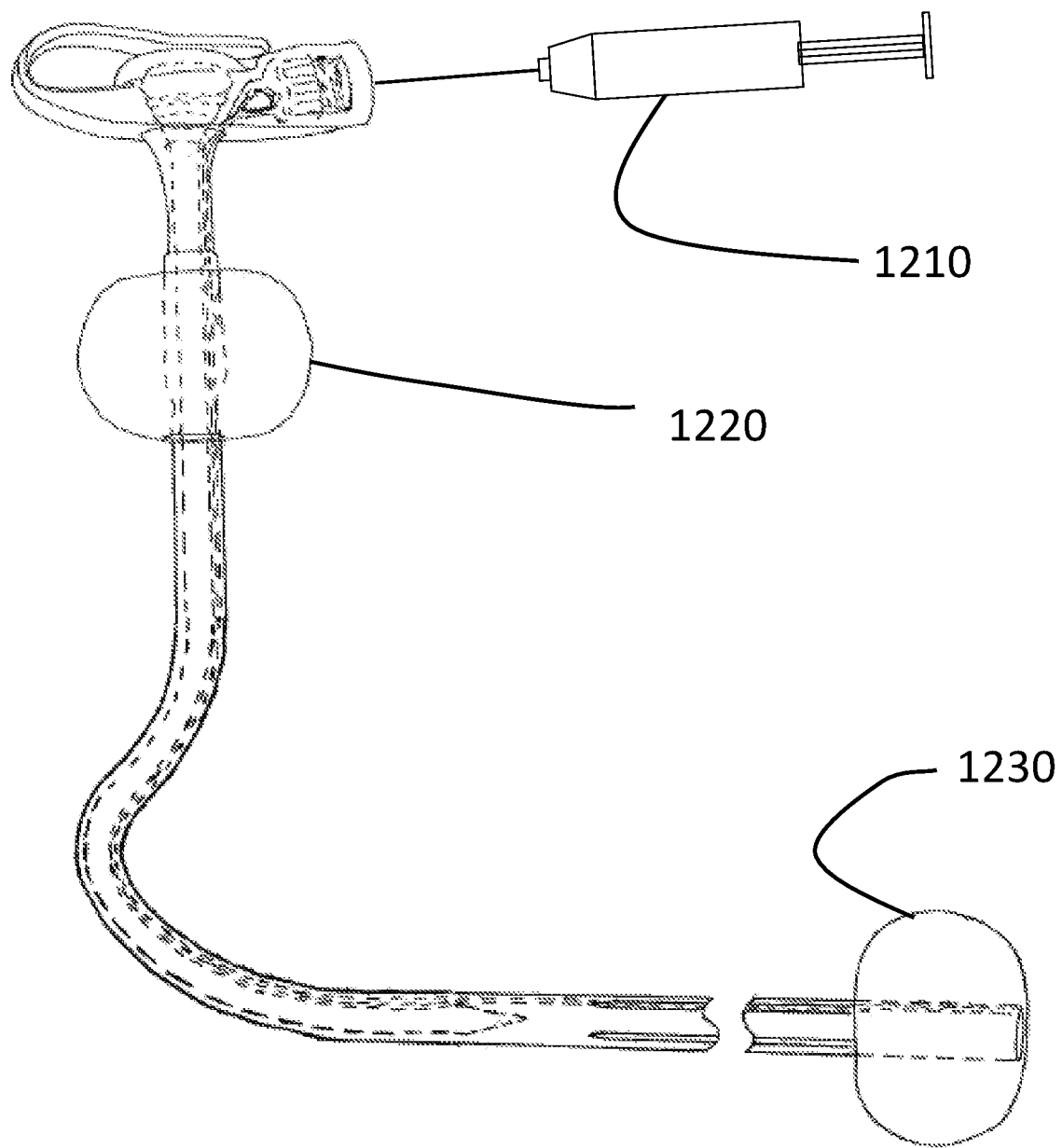
FIG. 12 illustrates inflation of anchor and float elements for one embodiment of this invention.

Now referring to FIG. 12, a source of pressurized gas, such as a syringe 1210 filled with air, carbon dioxide or nitrogen, or a pump unit is connected in fluid communication with the distinct lumen 505 of the collection element through the piercing of the silicone septum 835 within the inflation port access plug 1010.

The pressurized source of gas is utilized until the inflatable anchor has fully expanded 1220 and the inflatable float element has also expanded fully 1230.

Figure 13:
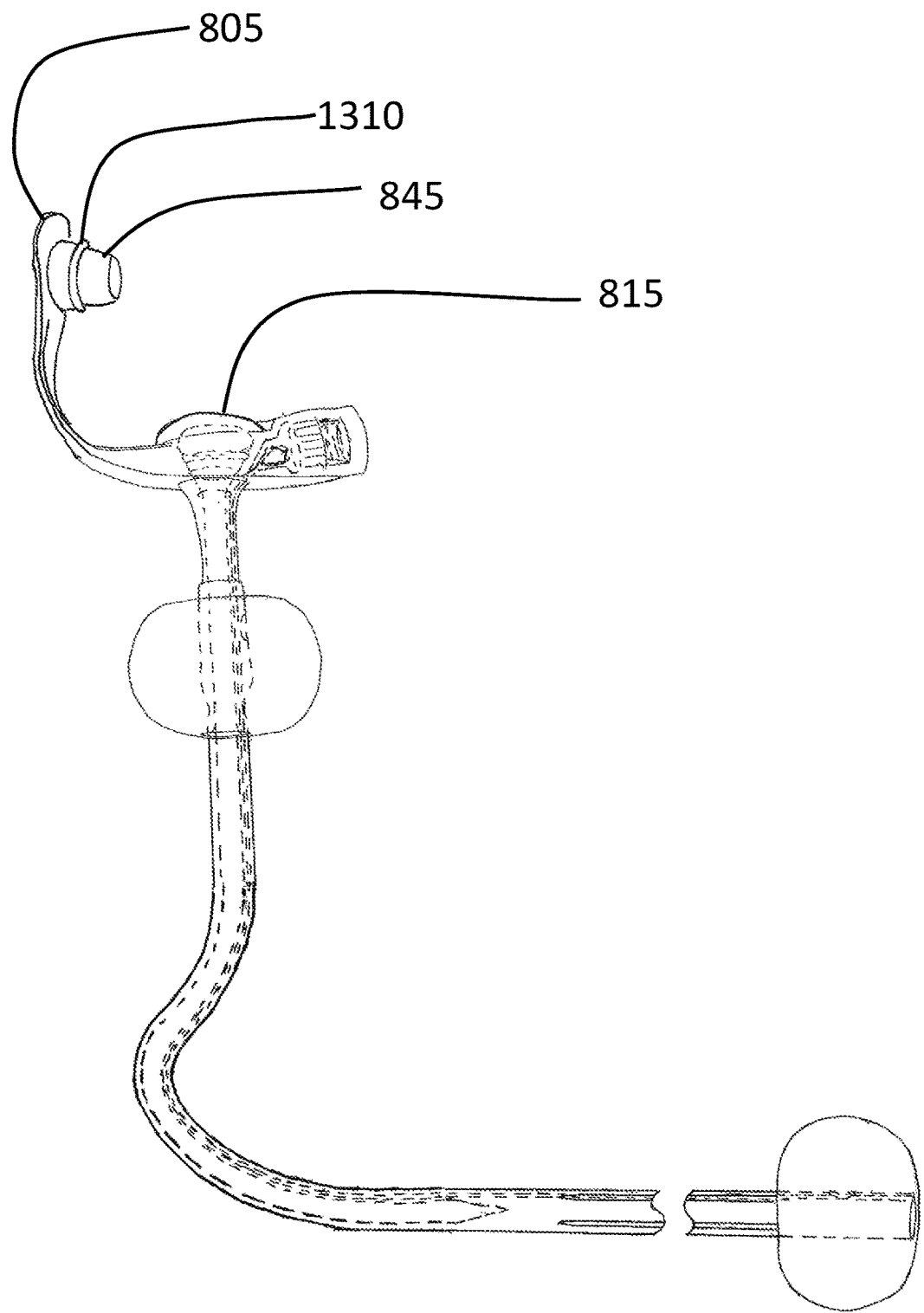
FIG. 13 depicts preparation for one embodiment of this invention prior to connection to a source of suction.

Referring to FIG. 13, the simplified extraction device can be utilized to remove at least a portion of the ingested food from within the patient's stomach through the removal of closure plug 845 from the upper port 815 by applying tension to the graspable extension flange 805. The applied tension forces the retention seal ring 1310 out of the upper port 815 and a source of suction similar to the disposal tube 600 previously described is inserted to the upper port to remove at least a portion of the contents from the patient's stomach. Upon completion of the extraction, the closure plug 845 is re-inserted into the upper port to seal the access to the stomach.

Figure 14:
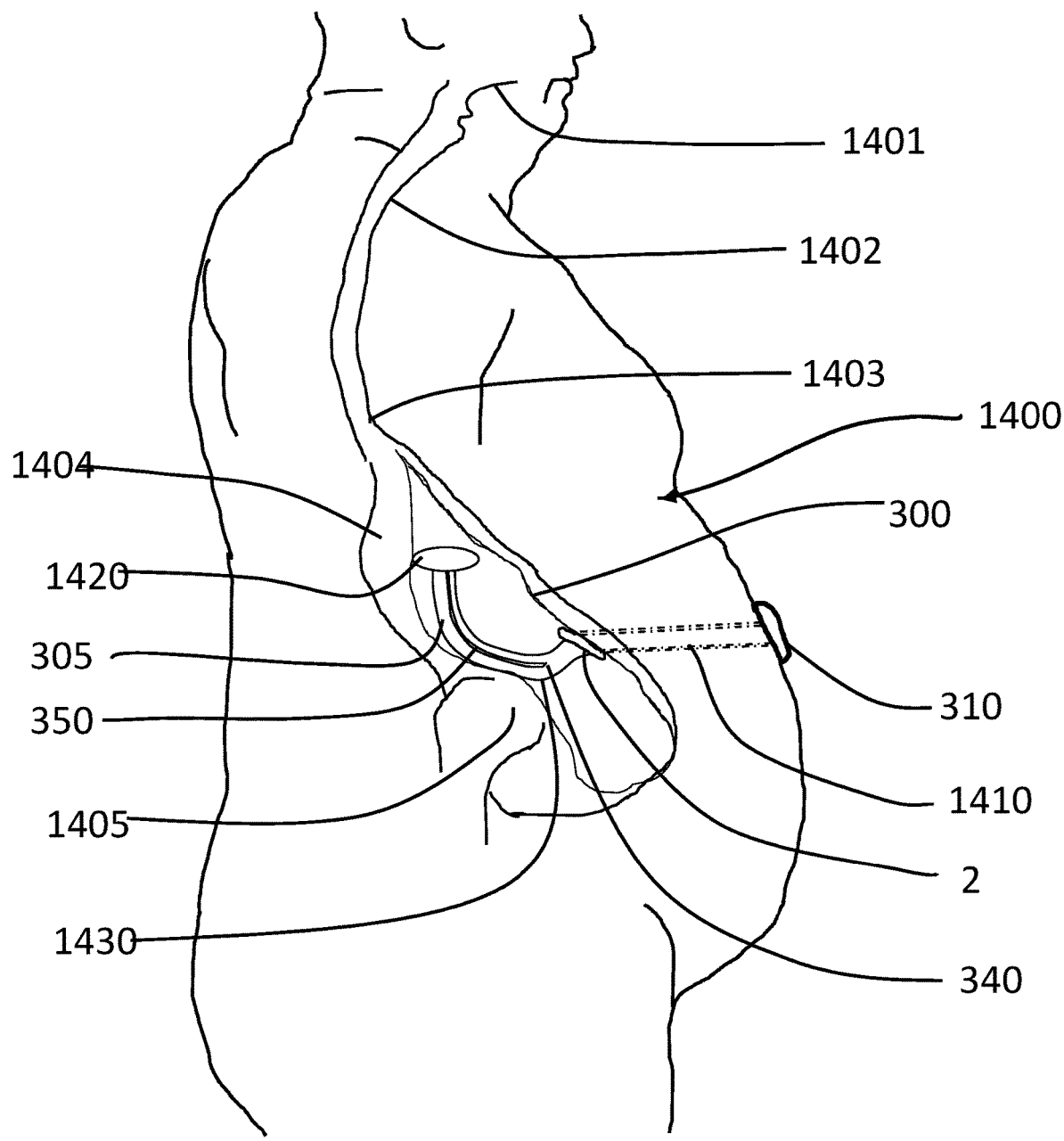
FIG. 14 illustrates a preferred deployment of the device of this invention.

Referring now the FIG. 14, deployed device 1400 is illustrated within an obese patient. An outline of the upper gastrointestinal tract is shown and extends from the base of the tongue 1401 into the esophagus 1402 and connects to the superior portion of the stomach 1404 at the lower esophageal sphincter 1403. The stomach extends to the pyloric valve 1405 which connects the distal end of the stomach to the proximal end of the duodenum.

The proximal portion of the collection element 305 extends into a superior position, or is directed towards the patients head, within the stomach. The proximal end of the preferred embodiment is produced with an inflatable member 1420 positioned to maintain the deployed collection element 305 in a slightly vertical orientation, or superior orientation, when the patient is standing. In this particular orientation, the collection channels 390 extend superiorly into the portion of the chyme within the stomach that is most recently ingested and may be easily solubilized through the imbibing of water after eating. The starches and sugars are readily solubilized and are capable of passing into the inner lumens of the collection channels 390. Due to the use of the narrow widths on the collection channels 390, coupled with the presence of water or other potable fluids that has been imbibed after eating, the lower viscosity slurry of the portion of the chyme that is easily solubilized, sugars, and or fine particulate starches that are easily dispersed within the solution, are preferentially separated and collected by the collection element. The poorly solubilized or large particulate material, such as fats or proteins or other complex foodstuffs, that have been poorly chewed and require further reduction prior to passing into the small intestine, remain within the stomach for reduction through the normal function of the stomach are prepared and passed through the pyloric valve for further digestion. The preferential separation of the high calorie sugars and starches within the stomach within the first 20 minutes of eating thereby provide a definitive target of timing for the patient to remove the portion of the ingested meal that is of low nutritional value and highly fattening. (Note, collection channel 390, not illustrated in FIG. 14) Further, the liquids and fine particulate passes along the inner collection element channels 390 through the aid of gravitational pull which enables these materials reach the transitional region of the collection element 340 where the applied negative relative pressure moves the collected material through the distal extension portion 1410 of the collection element. Additionally, in this particular orientation, solid or denser components of the chyme may collect near the antrum of the stomach for greater grinding and reduction in size through the normal action of the stomach without the interference of the collection element. The larger particles of food may not enter into the collection element due to the channel width preventing incursion of larger materials. As these larger particulates are not readily solubilized, they are most likely materials that are more complex in structure such as proteins, and other favorable food stuffs. Additionally, since the larger particulates cannot enter collection element 305, the internal channel elements 390 will not clog as is observed in devices with fenestrated tubes. The use of the long channels in the present invention do not facilitate localized negative pressure maintaining either large food particles or local internal stomach tissues against a discrete portion of the collection element, as happens with the fenestrated devices, since the negative pressure is not held in a discretely sealed and bounded location. The particular embodiment is produced intentionally with a slightly inflected portion 1430 that results in the fully hollow cylindrical portion of the device being oriented towards the antrum. In this configuration, fluids and fine particulate are able to collect within the fully enclosed portion of the hollow cylindrical portion thereby ensuring that the applied negative relative pressure is able to act fully upon collected fluids and particulate. Of course, the withdrawal of the collected fluid and fine particulates will occur when the patient is in an upright standing or sitting position. The skin mounted port/valve unit 310 is mounted to the anterior surface of the abdomen and is in fluid communication with the collection element 305.

The disclosed embodiment provides the means for the extraction of fluid with solubilized sugars and dispersed starches to enter within a free space of a device and to be transported away from the primary location of absorption. The transportation of a significant portion of the sugars and starches away from the site of absorption of the patient's gastrointestinal tract emulates the effect of correct food selection without the patient compliance issues typically seen in behavioral modification programs as well as ensures that malnutrition is not caused by the mass extraction of all types of food stuffs as is done with the prior art devices. Additionally, since the device is temporary in nature, and is delivered through an upper GI endoscopic approach, it may be retrieved as necessary or after patient behavior has been acceptably modified.

It should be understood that the foregoing disclosure and description of the present invention are illustrative and explanatory thereof and various changes in the size, shape and materials as well as in the description of the preferred embodiment may be made without departing from the spirit of the invention.

What is claimed is:

1. A device comprising:
    a) a channeled collection element having a longitudinal axis, a distal end and a proximal end, wherein the collection element further comprises a separate distinct lumen sealed at its proximal end and that runs substantially parallel to the longitudinal axis and for substantially the full length of the channeled collection element;
    b) at least one slot formed in the channeled collection element, said slot parallel to the longitudinal axis of the channeled collection element and sized to permit entrance into the channeled collection element of solubilized sugars or dispersed starches;
    c) a port or a port/valve assembly in fluid communication with the distal end of the channeled collection element;
    d) a shaping element for insertion into said separate distinct lumen;
    e) at least two inflation elements in fluid communication with said separate distinct lumen; and
    f) a plug for sealing said separate distinct lumen at its distal end while the shaping element is contained within said separate distinct lumen.

2. The device of claim 1 wherein the channeled collection element comprises multiple collection channels and a corresponding number of longitudinal slots formed in each channeled collection element.

3. The device of claim 2 wherein the multiple channeled collection elements transition to a non-slotted, single channeled collection element portion near the distal end of the channeled collection elements.

4. The device of claim 2 or 3 wherein the size of the slots range from 0.025 mm to 1.5 mm wide.

5. The device of claim 4, wherein the size of the slots range from 0.250 mm to 0.850 mm wide.

6. The device of claim 5, wherein the size of the slots are 0.400 mm wide.

7. The device of claim 3 wherein the single non-slotted channeled collection element portion contains a bend.

8. A method of extracting fluids rich in solubilized sugars and dispersed starches from a patient's gastrointestinal tract comprising the steps of:
    a) inserting into the stomach of the patient a device comprising:
        i. a channeled collection element having a longitudinal axis, a distal end and a proximal end, wherein the collection element further comprises a separate distinct lumen sealed at its proximal end and that runs substantially parallel to the longitudinal axis and for substantially the full length of the channeled collection element;
        ii. at least one slot formed in the channeled collection element, said slot parallel to the longitudinal axis of the channeled collection element and sized to permit entrance into the channeled collection element of solubilized sugars or dispersed starches;
        iii. a port or a port/valve assembly in fluid communication with the distal end of the channeled collection element;
        iv. a shaping element for insertion into said separate distinct lumen;
        v. at least two inflation elements in fluid communication with said separate distinct lumen; and vi. a plug for sealing said separate distinct lumen at its distal end while the shaping element is contained within said separate distinct lumen;
b) connecting to the port or port/valve assembly in fluid communication with the distal end of the channeled collection element a disposal tube; and
c) withdrawing fluid from the patient's stomach to a point external to the patient through the disposal tube.

9. The method of claim 8, wherein the channeled collection element comprises multiple collection channels and a corresponding number of longitudinal slots formed in each channeled collection element.

10. The method of claim 9, wherein the multiple channeled collection elements transition to a non-slotted, single channeled collection element portion near the distal end of the channeled collection elements.

11. The method of claim 10, wherein the single non-slotted channeled collection element portion contains a bend.

12. The method of claim 10, further comprising the step of inflating the inflation elements after the step of inserting the device into the patient's stomach but prior to the step of withdrawing fluids from the patient's stomach.

13. The device of claim 1, wherein one of the at least two inflation elements is located toward the distal end of the channeled collection element and the other of the at least two inflation elements is located toward the proximal end of the channeled collection element.

14. The method of claim 8, wherein the at least two inflation elements of the device comprises one of the at least two inflation elements being located toward the distal end of the channeled collection element and the other of the at least two inflation elements being located toward the proximal end of the channeled collection element.

\* \* \* \* \*